United States Patent [19]

Ruben

[11] Patent Number: 5,019,070
[45] Date of Patent: May 28, 1991

[54] UNDERGARMENT SHIELD

[76] Inventor: Margaret Ruben, 12 Longwood Dr., Saratoga, N.Y. 12866

[21] Appl. No.: 162,070

[22] Filed: Mar. 1, 1988

Disclaimer. The term of this patent subsequent to 01/28107 has been disclaimed.

[51] Int. Cl.⁵ .......................................... A61F 13/15
[52] U.S. Cl. .............................. 604/387; 604/379; 604/385.1
[58] Field of Search ........... 604/378, 379, 380, 385.1, 604/385.2, 387, 389, 390

[56] References Cited

U.S. PATENT DOCUMENTS

| | | | |
|---|---|---|---|
| 3,065,751 | 11/1962 | Gobbo | 604/379 |
| 3,211,147 | 10/1965 | Pherson et al. | 128/284 |
| 3,741,212 | 6/1973 | Schutte | 128/287 |
| 4,911,701 | 3/1990 | Mavinkurve | 604/385.2 |
| 4,205,679 | 6/1980 | Repke et al. | 604/385.2 |
| 4,333,466 | 6/1982 | Matthews | 128/290 R |
| 4,608,047 | 8/1986 | Mattingly | 604/387 |
| 4,624,666 | 11/1986 | DeRossett | 604/379 |
| 4,662,875 | 5/1987 | Hirutsu et al. | 604/389 |
| 4,678,464 | 7/1987 | Holtman | 604/379 |
| 4,685,915 | 8/1987 | Hasse et al. | 604/385.1 |
| 4,687,478 | 8/1987 | Van Tilburg | 604/387 |
| 4,701,178 | 10/1987 | Glaug | 604/389 |
| 4,758,240 | 7/1988 | Glassman | 604/379 |
| 4,762,521 | 8/1988 | Roessler et al. | 604/380 |
| 4,775,375 | 10/1988 | Aledo | 604/385.2 |
| 4,828,555 | 5/1989 | Hermansson | 604/379 |
| 4,940,462 | 7/1990 | Salerno | 604/385.2 |
| 4,944,735 | 7/1990 | Mokry | 604/385.2 |

Primary Examiner—C. Fred Rosenbaum
Assistant Examiner—Sharon Rose
Attorney, Agent, or Firm—Schmeiser, Morelle & Watts

[57] ABSTRACT

A disposable and anatomically reversible undergarment shield for removable attachment to the inside of underpants. The undergarment shield is shaped like an hourglass and has a thick portion which is reversible between a front side and a rear side, depending upon whether the wearer is a girl or a body. Words, colors, or other appropriate symbols are placed upon the end borders of the shield to indicate which side forms the front for a girl and likewise for a body. For more rapid and effective absorption, a generally Y-shaped trough is formed in the thick side of the shield. Gathers at the periphery of the crotch region ensure a close fit, thereby preventing leaks. Adhesive strips are used to attach the shield to the undergarment.

2 Claims, 2 Drawing Sheets

UNDERGARMENT SHIELD

FIELD OF THE INVENTION

The present invention relates generally to absorbent articles of clothing. More particularly, this inVention is an undergarment shield for removable attachment to the undergarment of a person suffering enuresis, especially a child having a bed-wetting problem.

BACKGROUND OF THE INVENTION

A common problem among young children is enuresis during sleep, commonly referred to as bed-wetting. After an episode in the middle of the night, the child suffering from this affliction usual awakens in extreme discomfort, feeling cold and wet. The child's clothing, sheets and sometimes even the blankets must be changed. Unfortunately, a single household usually has a limited supply of blankets and other bed linens, so that frequent washing is necessary. The problem, therefore, is not only uncomfortable and embarrassing for the child, but frustrating for parents as well.

Children suffering from enuresis often experience a lack of self confidence and self respect due to feeling like a "baby". As a result, social activities which involve spending a night at a friend's or a relative's house are usually avoided for fear of embarrassment.

A related problem is that of children who have "accidents" during the toilet training period. Although it is inconvenient and unpleasant to have to change a child who has wet his training pants at home, it is often impossible to do so when engaged in an activity outside the home. One temporary solution is to put a diaper on the child when leaving the house. Disadvantageously, alternating between the use of training pants and diapers can confuse the child, thus significantly extending the training period.

The present inventor has addressed the above-described problems and has posed a solution therefor by developing an undergarment shield for removable attachment to a child's undergarment. Thus, a child Who wets the bed during the night may sleep more comfortably Without worrying about soaking clothes, sheets, or blankets. Even if the child does aWaken after Wetting, only the shield, which is disposable, would be wet and it may possibly be replaceable by the child himself, depending upon the maturity of the child. In addition, the shield is designed so that no one but the wearer will be aware that the device is in place; that is, there is absent the characteristic bulkiness of a diaper. Advantageously, to further insure that only the shield becomes wet, the instant inventor has provided for the variable situs of wetting due to the anatomical differences between boys and girls using a single, reversible shield.

The major advantages of the invention are set forth in part herein and in part will be obvious herefrom, or may be learned by practice with the invention, the same being realized and attained by means of the instrumentalities and combinations pointed out in the appended claims.

SUMMARY OF THE INVENTION

The present invention is a disposable undergarment shield, particularly useful for children who have a bed-wetting problem or who are just being toilet trained, but adaptable to adults suffering from enuresis as well. In accordance with the present invention, the undergarment shield comprises an absorbent pad having a liquid impervious side for adhering to the undergarment worn by the child and a soft, absorbent side to be worn adjacent the child's body. The shield is of hourglass shape and is not bulky, so that only the wearer need be aware of its presence. Additionally, gathers are provided at the leg portions of the shield at the crotch region in order to more closely hold the shield against the wearer and to prevent leakage.

Either the front side or the rear side of the shield is thicker than the other in order to provide additional absorbent means where needed, depending upon whether the wearer is a girl or a boy. The present inventor provided for the varying locational effects of wetting caused by the anatomical differences between the sexes; in particular, it is well-known that a girl will produce more wetness at her rear side, whereas a boy tends to soak items of clothing worn toward his front side. Advantageously, the undergarment shield of the present invention is completely reversible, so that each one may be worn by either a boy or a girl. Conveniently located indicia on the inside of the shield enable the user to quickly determine which portion, thick or thin, should be worn at the front of the wearer.

To further enhance absorbency, a narrow and generally forked trough, which follows substantially the contour of the shield, is formed in the thick side of the shield.

Adhesive strips are provided on the water impervious side of the absorbent shield on order to secure the shield to the undergarment.

The accompanying drawings, referred to herein and constituting a part hereof, illustrate preferred embodiments of the invention, and together with the description, serve to explain the principles of the invention.

DETAILED DESCRIPTION OF THE DRAWINGS

Figures 1, 2:
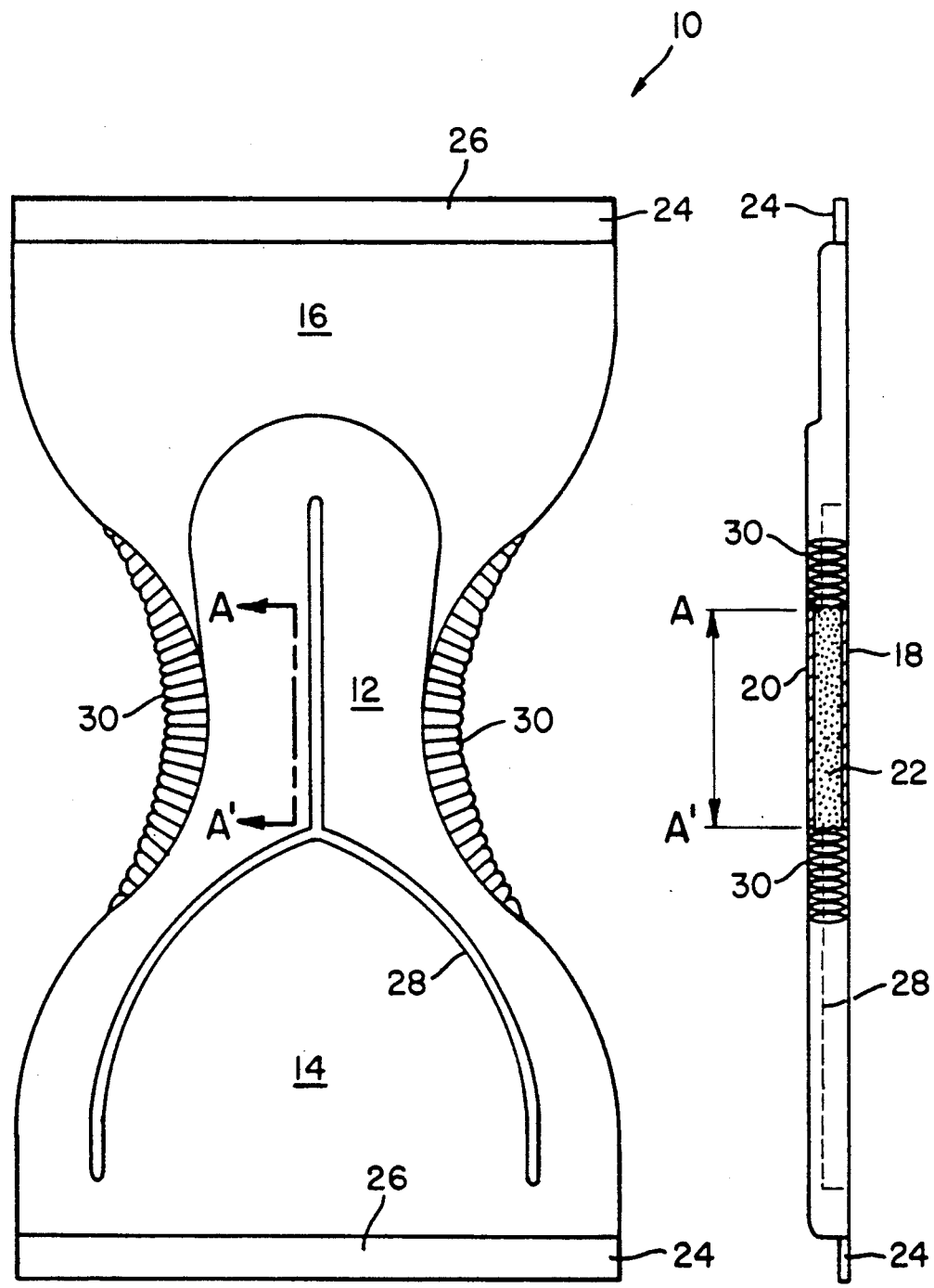
FIG. 1 is a front elevational view of the undergarment shield constructed in accordance with the present invention.
FIG. 2 is a partially cutaway side elevation of the undergarment shield of FIG. 1, taken along line A'-A.
Figure 3:
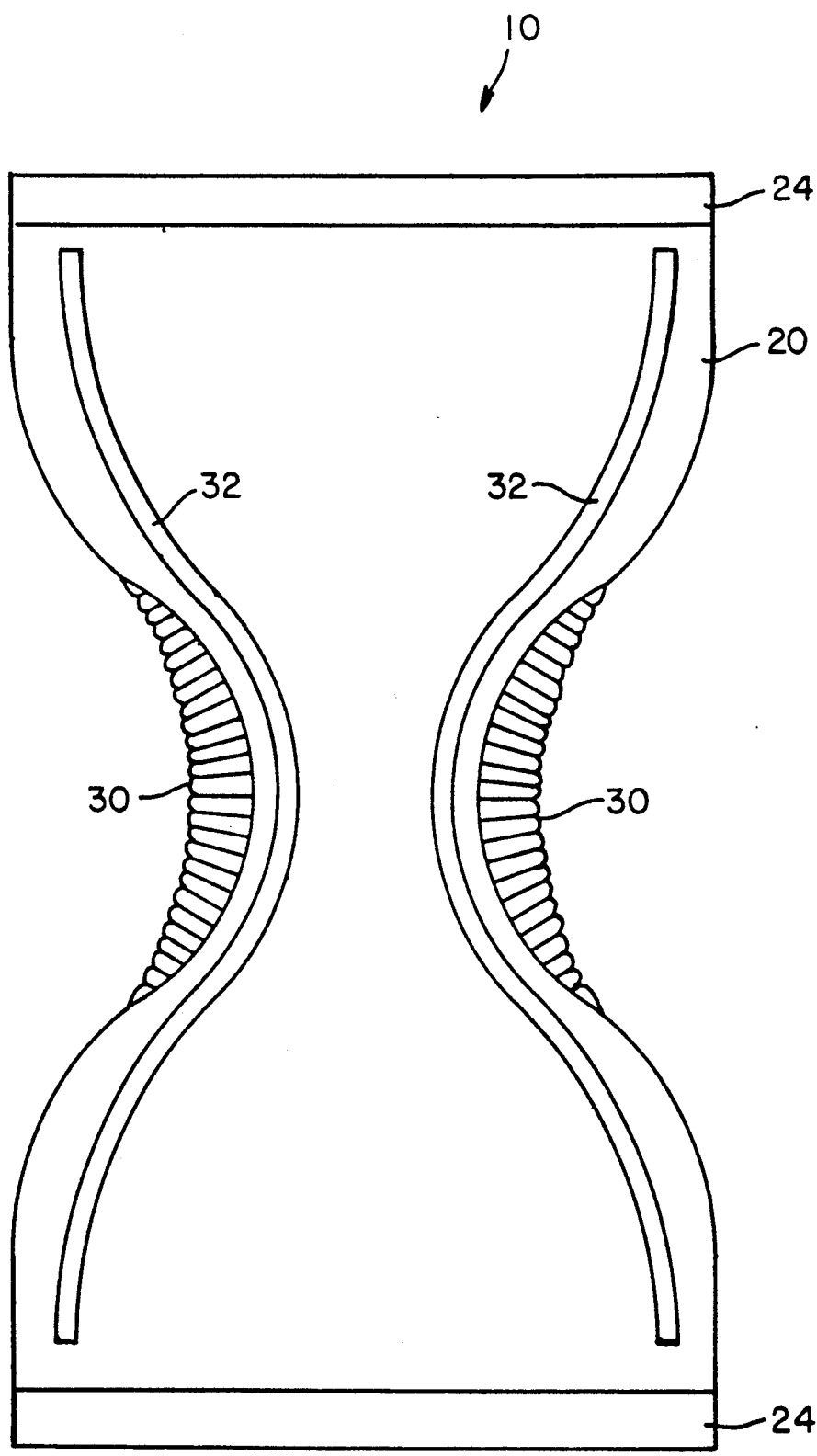
FIG. 3 is a back elevational view of the undergarment shield.

With reference to FIGS. 1 through 3, an undergarment shield constructed in accordance with the present invention is shown, generally designated by the numeral 10. As illustrated, the undergarment shield 10 is a pad of substantially hourglass shape for fitting entirely within a pair of underpants (not shown), having a narrow crotch region 12 and two wider regions 14 and 16 extending therefrom. As hereinafter described, the regions 14 and 16 are reversible between a body front and a body rear in order to achieve maximum absorbency, depending upon the sex of the wearer. The preferred embodiment of the undergarment shield 10 of the present invention comprises three plies: one ply of liquid impermeable fabric 20 overlaid by two plies of liquid absorbent composition 18 and 22, although only one layer of absorbent material is necessary to achieve the objectives of this invention. The absorbent top sheet or third ply 18 is made of a soft, liquid permeable material such as cotton, polyester, or polypropylene. In contrast, the bottom sheet or first ply 20 is comprised of a liquid impermeable fabric, such as a polyethylene film. The second ply 22 comprising absorbency enhancing means may be constructed of a variety of materials, which are capable of absorbing and retaining liquids, or a suitable combination thereof. These materials include, but are not limited to: foams, sponges, wood fibers, or cellulose wadding. In the preferred embodiment, a super-absorbent material, such as polyacrylate, is used.

One region 14, comprises a thick portion or more densely packed area of the undergarment shield 10. With respect to the wearer, this thick or denser portion 14 is reversible between the front and the rear of the body. The sex of the wearer determines the orientation of the shield 10 for achieving maximum absorbency. In particular, it has been observed that a boy who wears a diaper tends to significantly wet apparel toward the front of his body more than the rear; whereas a girl produces more wetness at the rear. Therefore, to account for the difference in levels of wetness at the body front or rear, depending upon the sex of the wearer, the undergarment shield 10 of the present invention has a thick or dense portion 14 which is placable next to the body area most demanding higher absorbency.

Borders 24 at opposite edges of the wider regions 14 and 16 of the undergarment shield 10 comprise the waist portion thereof. The borders 10 or waist bands are relatively narrow strips of material, preferably liquid impermeable, to which the third ply 18 and the first ply 20 are secured to each other by suitable means known to those versed in the art, encasing the absorbency enhancing means 22 therebetween. Indicia 26 are provided on the inside of the border 24 to aid the wearer or the applier of the invention to quickly determine which region, 14 or 16, should be placed at the body front of the wearer. In the preferred embodiment as shown in FIG. 1, the words "BOY FRONT" and "GIRL FRONT" are employed. However, any other appropriate indicia may be used, such as symbols of a boy and a girl, or colors like pink and blue. In this way, the wearer does not have to feel for the thick portion 14 and then remember which side goes in front. Indicia 26 thus provide a reliable way to guarantee that the shield 10 will be used to maximize absorbency. Alternative methods for identification include the selective placement of notches or the like. Additionally, as shown in FIG. 2, a forked or Y-shaped trough 28, having approximately the thickness of the thinner portion 16 of the shield 10, is provided to increase the absorbency rate by increasing the exposed surface area of the absorbency enhancing means where it is most needed, at the thick portion 14.

As shown in FIG. 1 and FIG. 3, gathers 30, along the outer periphery of the crotch region 12, ensure a closer fit around the legs of the wearer, thereby preventing leaks.

With reference to FIG. 3, two adhesive strips 32 for removably fixing the shield 10 to the inside of an undergarment are shown. Preferably, these strips 32 are located equidistantly from the edges of the shield 10 and follow its hourglass contour. The construction of these adhesive strips 32 is well known in the art, having removable, protective backing and being pressure-sensitive.

It is to be noted that the undergarment shield 10 of the present invention is constructed so as to fit entirely within an ordinary pair of underpants, without having the characteristic bulkiness of diapers. Additionally, the undergarment shield may be manufactured in different sizes, while maintaining the basic hourglass shape. For example, in one embodiment, to fit the typical undergarment of a girl, size 5, the dimensions are approximately: 13 inches total length, 7 inches border width, 2 inches width at the narrowest point in the crotch region, with the thick portion having a length of 9 inches.

It is further to be understood that the undergarment shield is adaptable for use by adults suffering from enuresis merely by making size alterations.

The invention in its broader aspects is not limited to the specific embodiments herein shown and described but departures may be made therefrom within the scope of the accompanying claims, without departing from the principles of the invention and without sacrificing its chief advantages.

What is claimed is:

1. A disposable, removably flexible, variably orientable and absorbent undergarment shield comprising:

an essentially planar, hour glass shaped pad having one ply of liquid impermeable fabric overlaid by at least one ply of liquid absorbent composition, said liquid impermeable ply and said liquid absorbent ply being marginally bound together, said hour glass shape being defined by a first wide region, a transitional narrow crotch region, the margins of said crotch region comprising gathers, and a second wide region having absorbency enhancing means therein, said second wide region being more absorbent that said first wide region said region wide region being thicker than said first wide region;

borders at opposite edges of the wider regions, said borders being liquid impermeable and secured to said one ply of liquid impermeable fabric and said at least one ply of liquid absorbent composition, said borders being identical such that said shield may be secured to the inside of an undergarment with said second wide region placed in registry with the body front or body rear of the wearer; and at least two adhesive strips located substantially equidistant from the edges of the shield, said strips being elongate and following said hour glass contour, said strips being of the type which are secured along one side and have a removable protective backing on the other side for revealing a pressure sensitive adhesive surface.

2. The invention of claim 1 further comprising a Y shaped trough located in said second wide region, the singular stem of said Y shaped trough extending through the transitional narrow crotch region, and the arms of said Y shaped trough extending outwardly therefrom into said second wide region, the depth of said Y shaped trough being substantially equal to the difference between the thickness of said first and second wide regions; and identifying indicia on at least one of said boarders to indicate the proper positioning of the wide regions.

* * * * *